United States Patent [19]
Lentle et al.

[11] Patent Number: 6,024,711
[45] Date of Patent: Feb. 15, 2000

[54] DIAGNOSIS OF OSTEOPOROSIS USING ACOUSTIC EMISSIONS

[75] Inventors: Brian C. Lentle, West Vancouver; John E. Aldrich, North Vancouver; Ainul Akhtar, Vancouver, all of Canada

[73] Assignee: The University of British Columbia, Vancouver, Canada

[21] Appl. No.: 09/038,850

[22] Filed: Mar. 12, 1998

[51] Int. Cl.[7] .................................................. A61B 7/00
[52] U.S. Cl. .......................................... 600/586; 600/587
[58] Field of Search ................................... 600/437, 442, 600/586, 587

[56] References Cited

U.S. PATENT DOCUMENTS

| | | | |
|---|---|---|---|
| 4,361,154 | 11/1982 | Pratt, Jr. | 600/587 |
| 4,437,473 | 3/1984 | Moll et al. | 600/586 |
| 4,754,763 | 7/1988 | Doemland | 600/587 |
| 4,799,498 | 1/1989 | Collier | 600/587 |
| 4,823,807 | 4/1989 | Russell et al. | 600/586 |
| 4,836,218 | 6/1989 | Gay et al. | 600/586 |
| 5,143,069 | 9/1992 | Kwon et al. | 600/437 |
| 5,749,363 | 5/1998 | Ishii et al. | 600/587 |
| 5,879,301 | 3/1999 | Chiabrera et al. | 600/437 |

FOREIGN PATENT DOCUMENTS

| | | |
|---|---|---|
| 4422451 | 12/1995 | Germany . |
| WO85045 | 10/1964 | WIPO . |

OTHER PUBLICATIONS

Failure Characteristics of Osteoporotic Vertebral Bodies Monitored by Accoustic Emision Hasegawa et al Spring 1993.

Mechanical Properties of Osteopenic Vertebral Bodies Monitored by Accoustic Emissions Hasegawa et al Bone 1993.

*Primary Examiner*—Cary O'Connor
*Assistant Examiner*—Charles Marmor, IV
*Attorney, Agent, or Firm*—C. A. Rowley

[57] ABSTRACT

Osteoporosis may be detected in-vivo by applying an acoustic sensor in contact with the skin of the patient while subjecting the patient to stress, for example, by lifting light weights and measuring the acoustic emissions sensed by the acoustic sensor to provide an indication of the degree of osteoporosis damage incurred by the bones of the patient being diagnosed.

20 Claims, 7 Drawing Sheets

DIAGNOSIS OF OSTEOPOROSIS USING ACOUSTIC EMISSIONS

FIELD OF INVENTION

The present invention relates to a test method for diagnosing osteoporosis, more particularly, the present invention comprises a method of detecting osteoporosis by sensing acoustic emissions.

BACKGROUND OF THE INVENTION

Osteoporosis is a disease involving considerable socio-economic implications in that it leads to hip fractures, vertebral fractures which cause severe pain and immobility and often result in surgery. The diagnostic test of choice for determining osteoporosis (prior to the present invention) is bone densitometry using a dual x-ray beam device, though it is also possible to use tests such as computed tomography CT and magnetic resonance imaging and/or ultra-sound measurements. None of these processes is of wide spread use due to the associated high cost of testing.

Dual energy x-ray absorption (DXA) and quantitative computed tomography (QCT) measure the electron density of bone which is almost entirely due to its calcium content. These procedures provide a measure of bone mass and thus an indication of whether the patient is suffering from osteoporosis since in osteoporosis there is a proportional loss of both matrix and material.

Quantitative ultra-sonography (QUS) is currently being investigated for use in the diagnosis of osteoporosis. This technique is based on the speed of transmission of the sound waves or signal transmitted by the bone.

The concept of using acoustic emissions for detecting bone damage such as cracks or for detecting the degree of wear in a joint has been described in German patent 442451 A1 published on Feb. 12, 1995. This describes applying a load to a bone and measuring the acoustic emission from the bone to assess the strength in the individual's bones being examined. The acoustic emission technique described in that German patent is used for determining the individual breaking load of human bone under mechanical load by evaluating the acoustic signals that are generated during crack formation or as generated in joints during movement. The patent states that for detecting cracks, analysis of the signal should be based on the peak amplitude of the signal generated and that for determining joint wear, i.e. during friction such as occurs in joints, the analyses should be based on the root mean square of the signal generated.

U.S. Pat. No. 4,836,218 issued Dec. 17, 1991 by Gray et al. describes a method of determining joint disorders by measuring acoustic emissions of the joint correlated with the position of the joint. (See also WO85/04564 published Oct. 24, 1985.)

U.S. Pat. No. 4,437,473 describes a technique for evaluating joints by detecting sounds generated by moving of the joints, in particular, analyzing acoustic emissions extending into the subsonic frequency ranges was found to be important to these diagnoses.

U.S. Pat. No. 4,823,807 issued Apr. 25, 1989 to Russell et al. is similar to technique of U.S. Pat. No. 4,437,473 discussed above in that it describes a method of examining for joint damage by defining an angle between two bones, angularly moving the bones while sensing the acoustic signals emitted from the joint between the bones during the relative angular movement and while applying a preselected resistance to the angular movement thereby stressing the joint.

Bones have been examined in-vitro and the differences identified between normal and osteoporotic (chemically digested) bones using acoustic emission techniques. See Hasegawa et al. "Failure Characteristics of Osteoporotic Vertebral Bodies Monitored by Acoustic Emission", Spine 1993, column 2314–2320 and/or Hasegawa et al "Mechanical Properties of Osteopenic Vertebral Bodies Monitored by Acoustic Emission", Bone 1993, 37–743. The use of acoustic emission to determine osteoporosis or the attempt to determine osteoporosis in vitro obviously is of no value in diagnosing osteoporosis in a patient.

The present diagnostic tests for osteoporosis are quite expensive and thus are not widely used as screening tools. The present invention provides an inexpensive, simple to use evaluation system for measurement of osteoporosis. Such testing if performed more routinely would result in treatment for the disease using drugs available for the purpose such as the biphosphonates, for the overall benefit of the patient and society.

BRIEF DESCRIPTION OF THE PRESENT INVENTION

It is an object of the present invention to provide an inexpensive, simple to use evaluation system for measurement of osteoporosis It is an object of the present invention to provide a method of detecting the degree of osteoporosis damage to bone using acoustic emissions.

Broadly, the present invention relates to a method to diagnose in vivo the degree of osteoporosis damage to a patient's bones comprising applying an acoustic sensor in sound receiving contact with the surface of the skin of said patient adjacent to a bone being tested, applying a preselected stress to said bone to generate an acoustic emission event from said bone, sensing the acoustic emission with said acoustic sensor to provide a sound signal and analyzing said sound signal to determine the extent, if any, of osteoporosis damage to said bone.

Preferably said acoustic emission event detected by said acoustic sensor will have a frequency in the range of 20 to 100 kHz.

Preferably, said analyzing of said signal to determine the extent, if any, of osteoporosis damage to said bone includes screening said sound signal to provide events with a ratio of energy/counts of $\leq 2$ and processing said events with a ratio of energy/counts of $\leq 2$ to define their total energy and provide a measure of severity of osteoporosis.

Preferably said total energy of said events with a ratio of energy/counts of $\leq 2$ is screened to review events with the equivalent of an accumulated energy of greater than 200 for amplification of the signal by 40 dB.

Preferably, said stress is applied by said patient lifting a weight from a rest position wherein said weight is supported to an elevated position

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
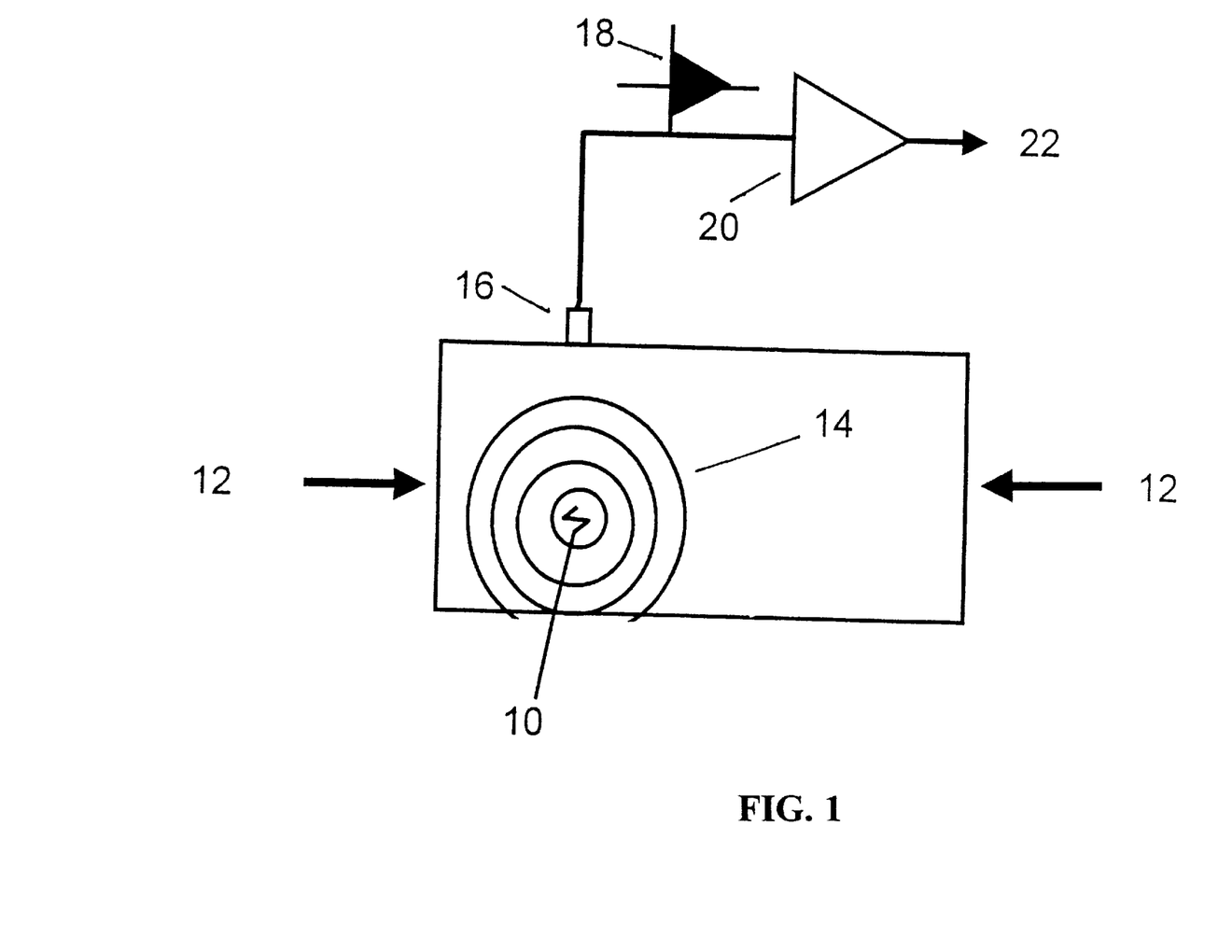
FIG. 1 shows the basic principle of acoustic imaging testing system.

Before describing the method of the present invention in detail, the basic concept of acoustic emissions sound wave analysis is illustrated in FIG. 1. As illustrated, the source 10, i.e. the material or person being tested (it is subject to applied stress as indicated at 12) which generates an acoustic emission as schematically represented by the circles 14. An acoustic sensor 16 detects the sound waves 14 and produces an electrical signal representing the sound waves detected by the sensor 16 which normally is amplified by a preamplifier 20 (positioned close to the sensor 16) and is delivered as a signal 18 (sound signal) to the detection and measurement electronics schematically represented by the arrow 22.

This type of non-destructive testing has been applied as above described to many different applications.

Figure 2:
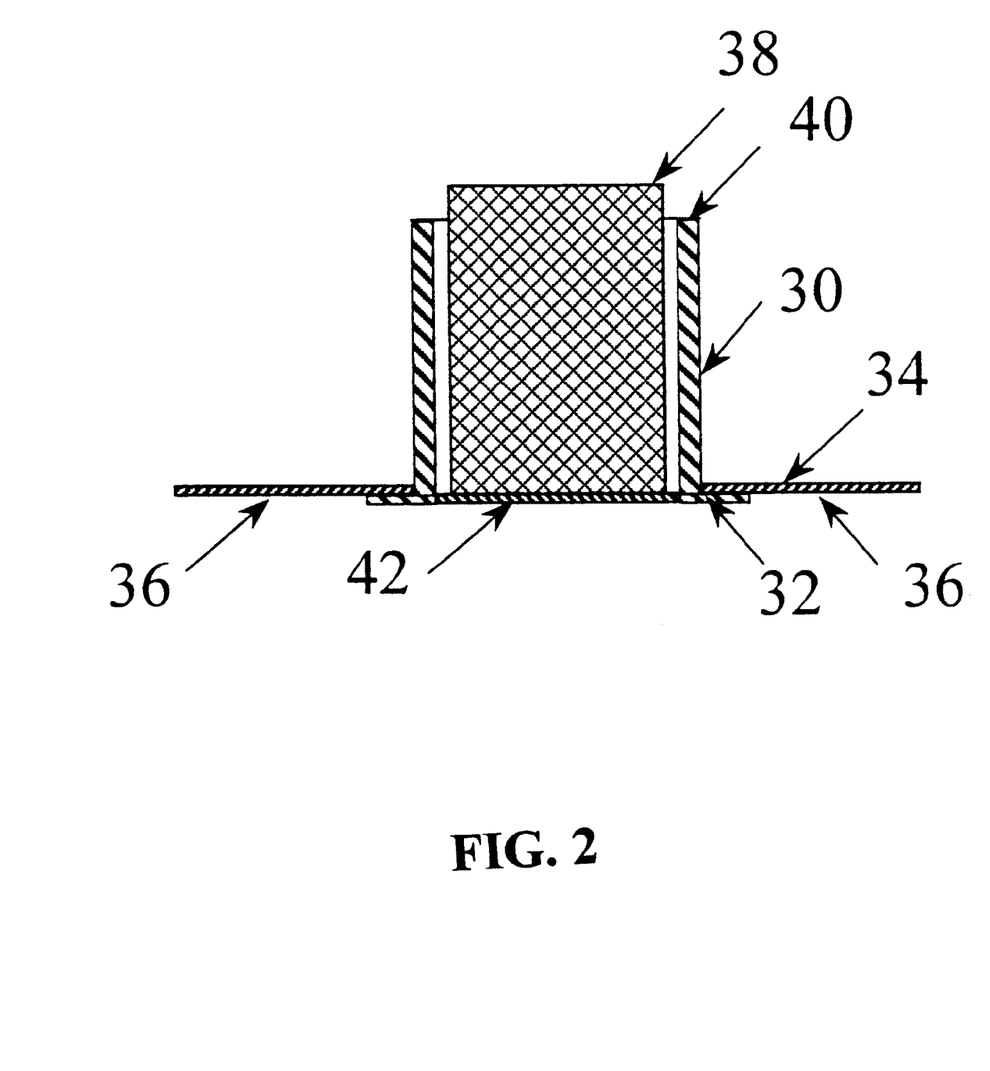
FIG. 2 is a cross-section of a mounting system for mounting an acoustic sensor onto the body of the patient being tested.
Figure 3:
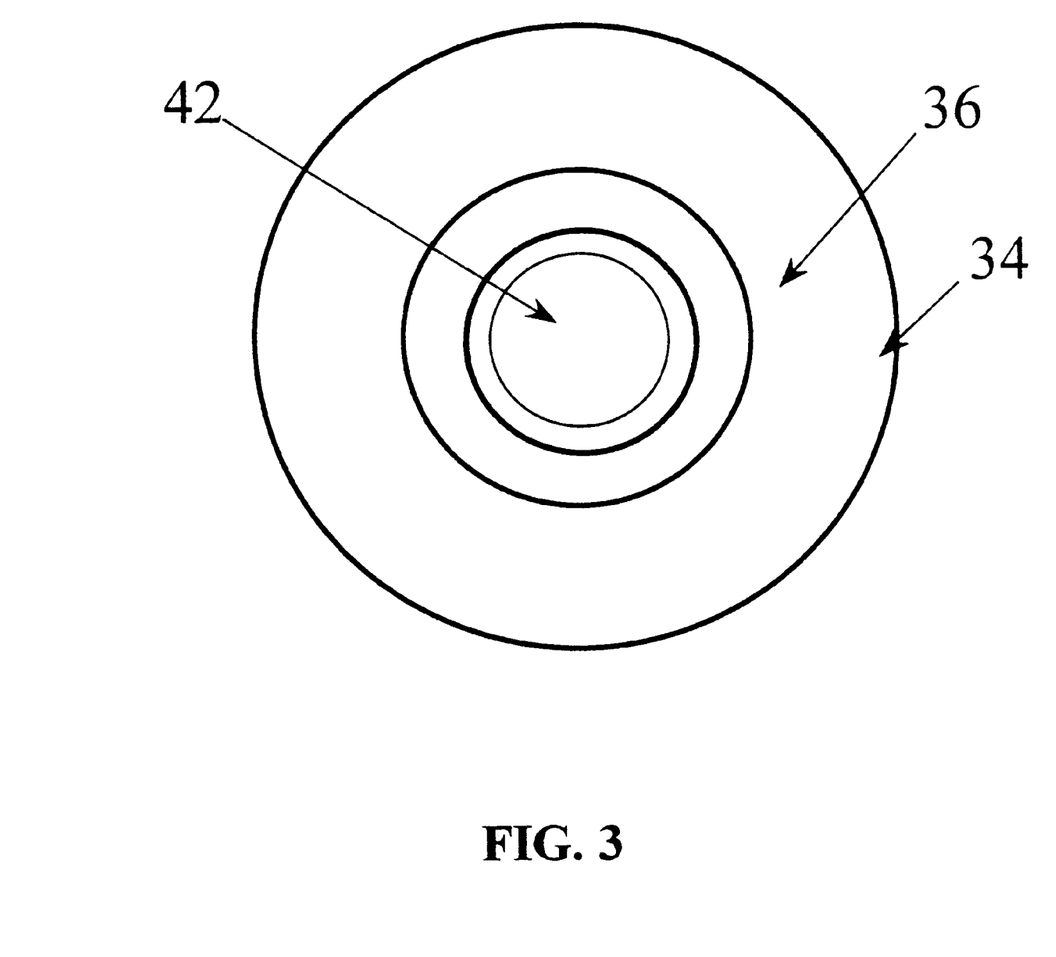
FIG. 3 is a view looking up from the bottom in FIG. 2.

To determine whether or not acoustic emissions could be used to detect osteoporosis, it was necessary to provide a system for mounting the acoustic sensor on the skin and coupling the acoustic sensor with the skin effectively so that signals generated due to osteoporosis could be detected. The device adopted for this purpose is shown in FIGS. 2 and 3 is composed as illustrated of a cylindrical holder 30 having a substantially radial flange 32 which underlies an annular self-adhesive pad 34 that connects the cylindrical holder 30 to the pad 34 and the pad is adhered to the skin via the adhesive layer 36 on the surface thereof A cylindrical shaped acoustic sensor 38 is received within the cylindrical sleeve 30 as a snug fit. In the schematic drawings of FIGS. 2 and 3 the space 40 between the inner surface of the holder 30 and the adjacent face of sensor 38 has been exaggerated. An adhesive tape (not shown) is normally applied over the distal end of the sensor 38 and is used to better hold the sensor in place on the patient.

A suitable acoustic gel 42 is applied to the surface of the sensor 38 between the sensor and the surface of the skin of the patient being tested. This acoustic gel facilitates the transmission of sound waves from the body, i.e. from the skin of the subject to the sensor 38 so that the available signal is still sufficient for its intended purpose.

A suitable sensor for use in practice the present invention is a piezoelectric transducer having a frequency range of between 20–100 kHz with resonance at about 60 kHz. The frequency range selected enables signals associated with osteoporosis to be transmitted to the sensor without undue attenuation, while keeping noise from non relevant sources to a minimum. For example an RG sensor supplied by Physical Acoustics Corporation (New Jersey) having a diameter of 17.5 mm. meets those requirements.

Figure 4:
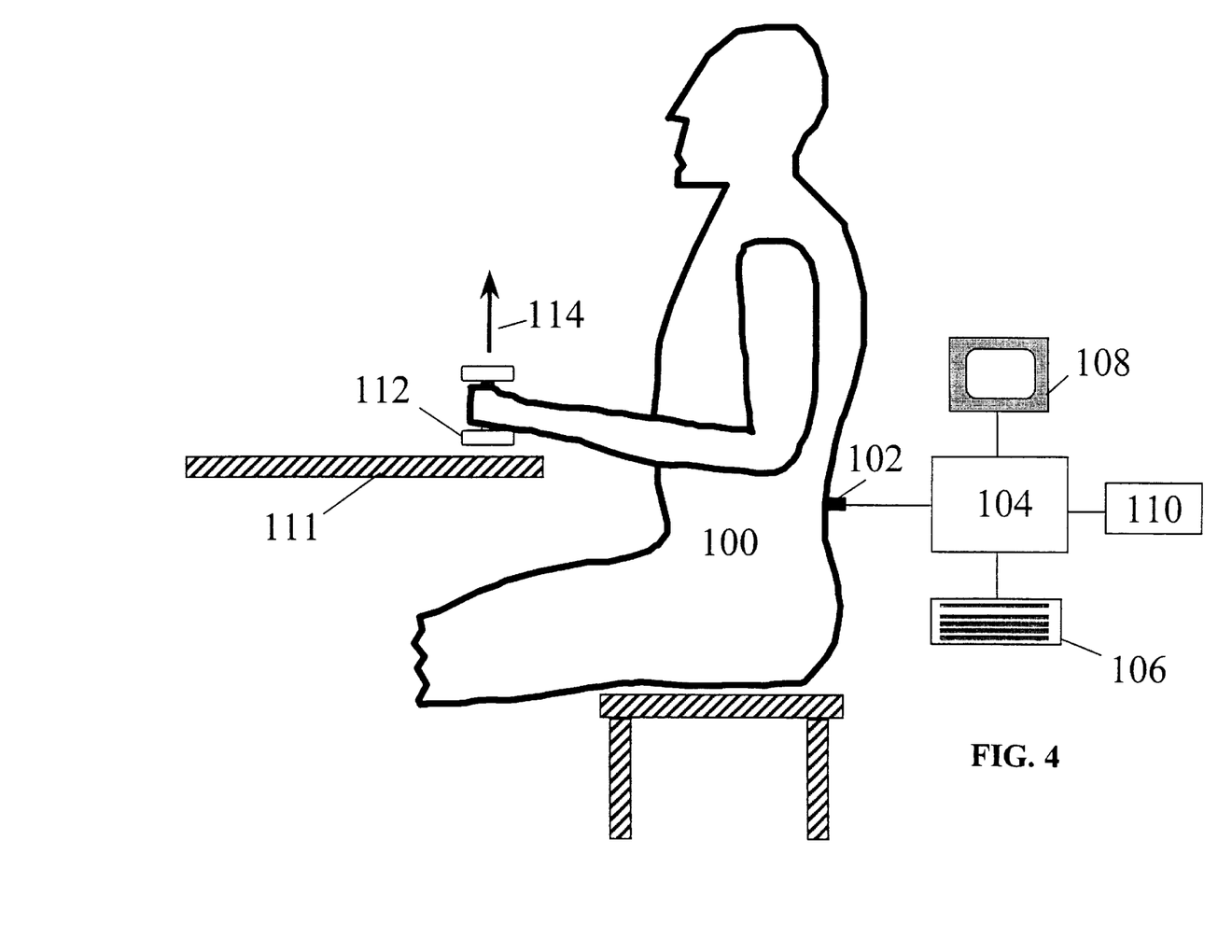
FIG. 4 is a schematic illustration of the application of the present invention to a patient.

As shown in FIG. 4, in practice the present invention the patient 100 is fitted with a sensor 102, i.e. preferably using the mounting system shown in FIGS. 2 and 3 (the sensor 38 described above and the sensor indicated at 102 are equivalents). The sensor 102 delivers the signals sensed by the sensor 102 and amplified by a preamplifier (not shown but equivalent to the preamplifier 20 described above) to a computer 104 (equivalent to the measurement electronics schematically represented by the arrow 22 in FIG. 1) having an input keyboard 106 and a display 108 to display the results obtained. Obviously, the computer 104 may also be connected to a suitable printer as indicated at 110 or any other suitable output device.

In order to carry out the present invention, the subject 100 provided with a bar bell or a pair of bar bells or the like 112 and is instructed to raise the bar bells as indicated by the arrow 114 off a stationary support surface 111. The acoustic emission sensed with the weight(s) 112 at rest on the surface 111 provides an indication of background and the lifting of bar bell or weights 112 applies stress to the bone and results in an acoustic emission being generated by the bones of the patient 100 and these acoustic emissions are detected by detector or sensor 102. The sensors are preferably positioned at lumbar vertebra 1 or 2 (L1 or L2) as these are the bones where the DXA measurements are made, however the sensor may be positioned to sense the acoustic emissions of any suitable bone under stress.

Figure 5:
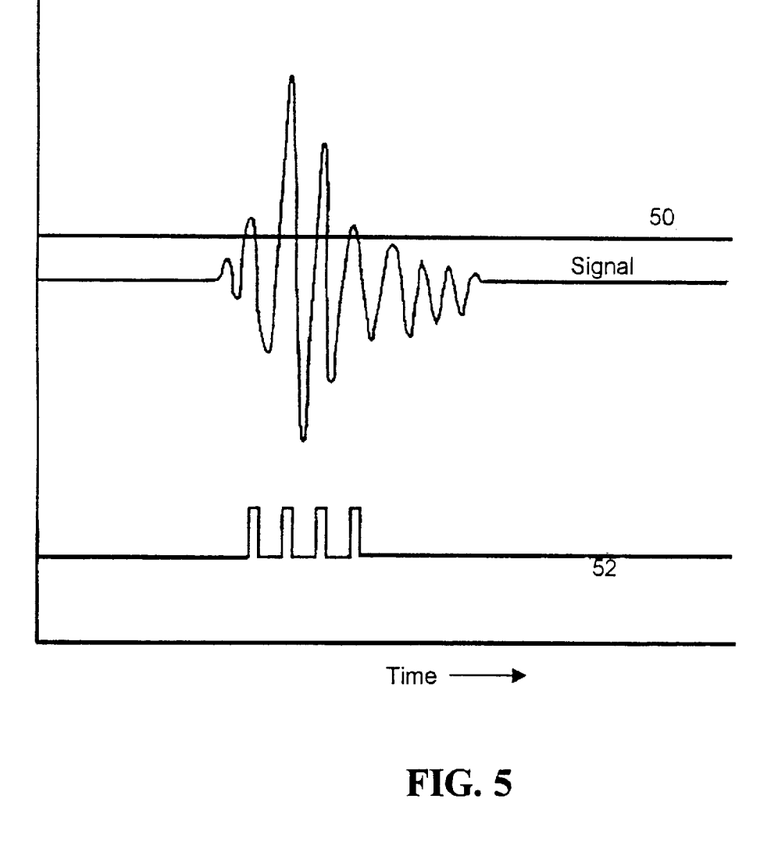
FIGS. 5 and 6 show a typical signal and the various characteristics that may be measured
Figure 6:
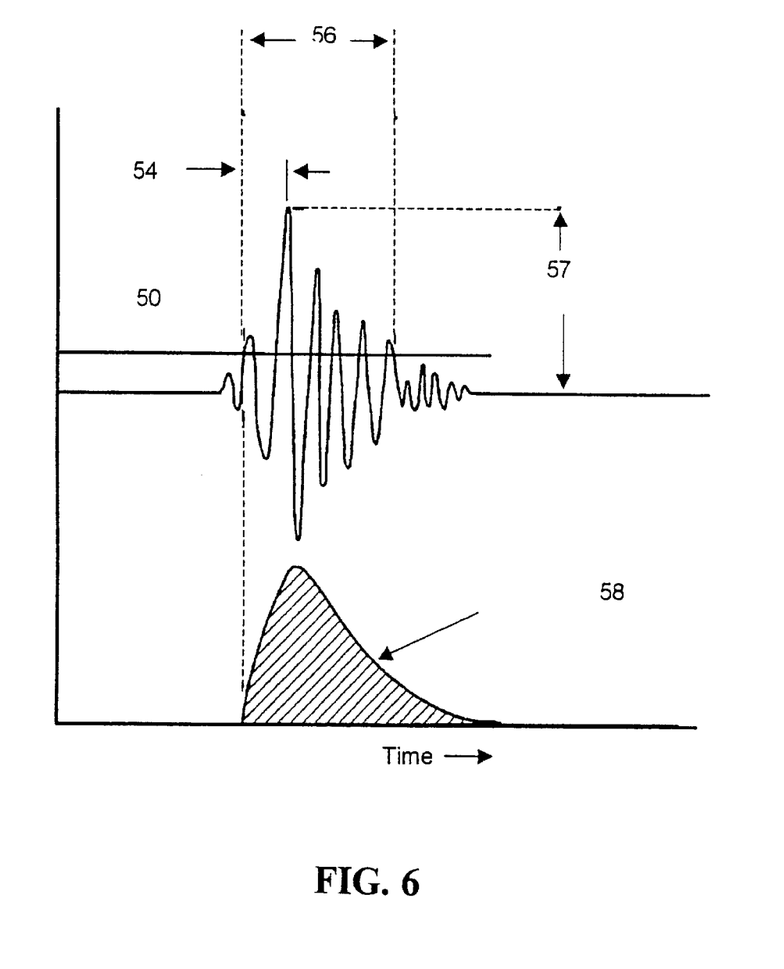

The acquired burst-type acoustic emission signal is amplified using the preamplifier 20 which was placed in close proximity to the sensor 102 (38). The preamplifier 20 was set at selected amplification of about 30 dB to 60 dB and the signal threshold was set as indicated at 50 (FIG. 5 and 6) for data acquisition at about 10 dB below the degree of amplification. The signal as indicated in FIG. 5 may be analyzed to determine the threshold crossing pulses also known as threshold crossings or counts 52. FIG. 6 shows the other commonly used parameters obtained from the burst type acoustic emission. They are rise time 54, duration 56, amplitude 57 and MARSE or energy 58. The measured area under the rectified signal envelope (MARSE or energy) remains sensitive to amplitude 57 and duration 56, but remains less dependent on the threshold setting 50 and operating frequency.

The cumulative energy obtained through the in-vivo acoustic emission testing was compared with X-ray Bone Mineral Density (BMD-L1), the latter also measured in-vivo using the conventional Dual Energy X-ray Analysis (DXA). The BMD-L1 was examined in relation to the Cumulative Energy for time periods ranging from 3 seconds to 30 seconds from the start of the acoustic emission test. It was found that the correlation between Cumulative Energy and BMD L1 was best during the early stage of the load hold i.e. a period of less than about 5 seconds from commencement of the acoustic emission test.

Figure 7:
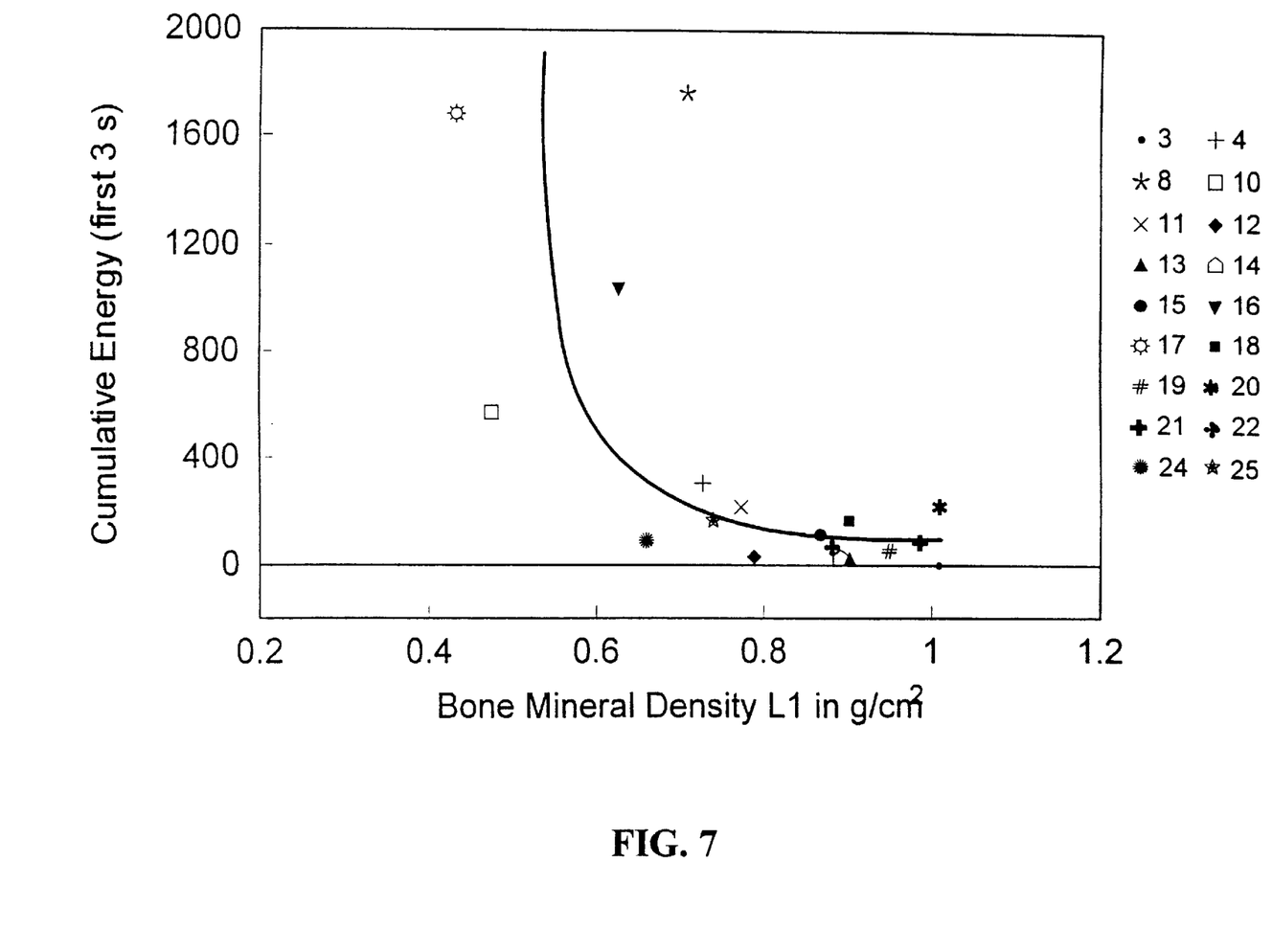
FIG. 7 is a plot of accumulated energy versus bone mineral density (BMD) and demonstrates the results obtained for 17 different patients whose bone density was known, i.e. degree of osteoporosis was known.

FIG. 7 is a plot of Cumulative Energy during the first 3 seconds of the acoustic emission test vs. X-ray Bone Mineral density (both measured in vivo) and clearly shows that the Cumulative Energy obtained during the first 3 seconds of the acoustic emission test increases with a decrease in the X-ray Bone Mineral Density.

A comparison was made of acoustic emission events obtained from persons having had no prior known history of osteoporosis with those obtained from persons having osteoporosis as diagnosed through dual energy X-ray absorption (DXA). It was found that many acoustic emission events having ratios of energy/counts greater than 2 (>2) were common to both. Hence such signals (energy/count >2) were considered not relevant to osteoporosis.

Events having energy/count ratios of less than or equal to 2 (<2) were also present in both categories of the subjects examined. However, subjects with no known history of osteoporosis produced either only a few or no events with energy/count ≦2. Subjects with a known history of osteoporosis (diagnosed through DXA) produced many events having energy/count ≦2 and therefore events with energy/count ≦2 are considered relevant to osteoporosis. A filtering criteria is used to remove events having energy/count >2 and the filtered events with energy/count ≦2 is used to characterize osteoporosis.

MARSE or energy (58 in FIG. 6) is used to characterize the severity of the osteoporosis. MARSE or energy associated with all events having energy/count ≦2 were added to obtain "cumulative energy" (plotted on the Y or vertical axis of FIG. 7). This parameter (cumulative energy) obtained from acoustic emission testing produced similar results to those obtained with the conventional DXA test method (FIG. 7).

EXAMPLE

In order to determine the effectiveness of the present invention in detecting osteoporosis, a number of different subjects having varying degrees of osteoporosis were subject to a test as follows:

The patients were seated on a backless stool and a single piezoelectric detector (17.5 mm in diameter) was attached as above described with acoustic gel interposed between the patient and the sensor on the posterior of one of the lumbar vertebrae (the vertebrae conventionally designated L1). With the sensor so positioned the patient was made to lift two 1.5 kg weights from a rest position i.e. weight on the support 111 with the arms substantially horizontal through an elbow movement of about 90 degrees.

The acquired signal was amplified using the preamplifier 20 which was placed in close proximity to the sensor 102 (38) which was in the L1 position. The preamplifier was set at 40 dB and the signal threshold was set at 30 dB for data acquisition. The signal was analyzed to measure the rise time, counts (threshold crossings), energy, duration and amplitude and the energy and the counts where used as the ratio energy/counts to define cumulated energy as presented in FIG. 7.

The signals generated by different patients having different degrees of osteoporosis were analyzed based on the criterion of the ratio of energy/counts of equal to or less than 2 i.e. ≦2.

As shown in FIG. 7 when the accumulated energy measured exceed about 200 units (based on amplification of the signal in the preamplifier 20 of 40 dB), the bone mineral density was significantly less than 0.8 g/cm$^2$ which is generally accepted as indicating clinical osteoporosis in all patients Having described the invention, modifications will be evident to those skilled in the art without departing from the scope of the invention as defined in the appended claims.

We claim:

1. A method to diagnose in vivo osteoporosis damage to a patient's bones comprising applying an acoustic sensor in sound receiving contact with the surface of the skin of said patient adjacent to a bone being tested, applying a preselected stress to said bone to generate an acoustic emission event from said bone, sensing the acoustic emission with said acoustic sensor to provide a sound signal and analyzing said sound signal to determine the extent, if any, of osteoporosis damage to said bone.

2. A method to diagnose in vivo osteoporosis damage to a patient's bones as defined in claim 1 wherein said acoustic emission event detected by said acoustic sensor has a frequency in the range of 20 to 100 kHz.

3. A method to diagnose in vivo osteoporosis damage to a patient's bones as defined in claim 2 wherein said analyzing said signal to determine the extent, if any, of osteoporosis damage to said bone includes screening said sound signal to provide events with a ratio of energy in said signal (energy)/number of times said signal crosses a threshold (counts) of ≦2.

4. A method to diagnose in vivo osteoporosis damage to a patient's bones as defined in claim 3 wherein said applying stress comprises said patient lifting a weight from a rest position wherein said weight is supported to an elevated position.

5. A method to diagnose in vivo osteoporosis damage to a patient's bones as defined in claim 2 wherein said analyzing said signal to determine the extent, if any, of osteoporosis damage to said bone further includes processing said events with a ratio of energy in said signal (energy)/number of times said signal crosses a threshold (counts) of ≦2 to define their total energy and provide a measure of severity of osteoporosis.

6. A method to diagnose in vivo osteoporosis damage to a patient's bones as defined in claim 5 wherein said total energy is based on energy over a 3 second period at commencement of sensing said acoustic emission.

7. A method to diagnose in vivo osteoporosis damage to a patient's bones as defined in claim 6 wherein said total energy of said events with a ratio of energy/counts of ≦2 is screened to review events with the equivalent of an accumulated energy of greater than 200 for amplification, of the signal by 40 dB.

8. A method to diagnose in vivo osteoporosis damage to a patient's bones as defined in claim 7 wherein said applying stress comprises said patient lifting a weight from a rest position wherein said weight is supported to an elevated position.

9. A method to diagnose in vivo osteoporosis damage to a patient's bones as defined in claim 6 wherein said applying stress comprises said patient lifting a weight from a rest position wherein said weight is supported to an elevated position.

10. A method to diagnose in vivo osteoporosis damage to a patient's bones as defined in claim 5 wherein said applying stress comprises said patient lifting a weight from a rest position wherein said weight is supported to an elevated position.

11. A method to diagnose in vivo osteoporosis damage to a patient's bones as defined in claim 2 wherein said applying stress comprises said patient lifting a weight from a rest position wherein said weight is supported to an elevated position.

12. A method to diagnose in vivo osteoporosis damage to a patient's bones as defined in claim 1 wherein said analyzing said signal to determine the extent, if any, of osteoporosis damage to said bone includes screening said sound signal to provide events with a ratio of energy in said signal (energy)/number of times said signal crosses a threshold (counts) of ≦2.

13. A method to diagnose in vivo osteoporosis damage to a patient's bones as defined in claim 12 wherein said applying stress comprises said patient lifting a weight from a rest position wherein said weight is supported to an elevated position.

14. A method to diagnose in vivo osteoporosis damage to a patient's bones as defined in claim 1 wherein said analyzing said signal to determine the extent, if any, of osteoporosis damage to said bone further includes processing said events with a ratio of energy in said signal (energy)/number of times said signal crosses a threshold (counts) of ≦2 to define their total energy and provide a measure of severity of osteoporosis.

15. A method to diagnose in vivo osteoporosis damage to a patient's bones as defined in claim 14 wherein said total energy is based on energy over a 3 second period at commencement of sensing said acoustic emission.

16. A method to diagnose in vivo osteoporosis damage to a patient's bones as defined in claim 15 wherein said total energy of said events with a ratio of energy/counts of ≦2 is screened to review events with the equivalent of an accumulated energy of greater than 200 for amplification of the signal by 40 dB.

17. A method to diagnose in vivo osteoporosis damage to a patient's bones as defined in claim 16 wherein said applying stress comprises said patient lifting a weight from a rest position wherein said weight is supported to an elevated position.

18. A method to diagnose in vivo osteoporosis damage to a patient's bones as defined in claim 15 wherein said applying stress comprises said patient lifting a weight from a rest position wherein said weight is supported to an elevated position.

19. A method to diagnose in vivo osteoporosis damage to a patient's bones as defined in claim 14 wherein said applying stress comprises said patient lifting a weight from a rest position wherein said weight is supported to an elevated position.

20. A method to diagnose in vivo osteoporosis damage to a patient's bones as defined in claim 1 wherein said applying stress comprises said patient lifting a weight from a rest position wherein said weight is supported to an elevated position.

* * * * *